United States Patent
Sugizaki

(10) Patent No.: US 11,169,151 B2
(45) Date of Patent: Nov. 9, 2021

(54) DETECTION DEVICE AND DETECTION METHOD

(71) Applicant: Kabushiki Kaisha Toshiba, Minato-ku (JP)

(72) Inventor: Yoshiaki Sugizaki, Fujisawa (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 350 days.

(21) Appl. No.: 15/913,946

(22) Filed: Mar. 7, 2018

(65) Prior Publication Data

US 2019/0154687 A1    May 23, 2019

(30) Foreign Application Priority Data

Nov. 17, 2017  (JP) ............... JP2017-221876

(51) Int. Cl.
  *G01N 33/569*  (2006.01)
  *G01N 33/566*  (2006.01)
  *G01N 33/559*  (2006.01)
  *G01N 33/483*  (2006.01)

(52) U.S. Cl.
  CPC ..... *G01N 33/56983* (2013.01); *G01N 33/483* (2013.01); *G01N 33/559* (2013.01); *G01N 33/566* (2013.01)

(58) Field of Classification Search
  CPC .......... G01N 33/56983; G01N 33/483; G01N 33/559; G01N 33/566; G01N 2333/95; G01N 2333/811; G01N 2333/96438; G01N 2333/96433; G01N 29/036; G01N 29/022; G01N 29/00; G01N 2291/0426; G01N 2291/0423; G01N 2291/0255; G01N 2291/0256; G01N 2333/11; B82Y 30/00
  See application file for complete search history.

(56) References Cited

U.S. PATENT DOCUMENTS 9,645,135 B2  5/2017  Shin et al.
2013/0288922 A1 * 10/2013  Miller .................. G01N 21/211
                                                                506/9

(Continued)

FOREIGN PATENT DOCUMENTS

EP  3 244 210 A1  11/2017
JP  6-508438 A    9/1994

(Continued)

OTHER PUBLICATIONS

Racaniello et al, May 5, 2009 ("Influenza virus attachment to cells: role of different sialic acids" website accessed on Apr. 13, 2020: https://www.virology.ws/2009/05/05/influenza-virus-attachment-to-cells-role-of-different-sialic-acids/) (Year: 2009).*

(Continued)

*Primary Examiner* — Dennis White
(74) *Attorney, Agent, or Firm* — Obion, McClelland, Maier & Neustadt, L.L.P.

(57) ABSTRACT

According to one embodiment, a detection device includes a sensor element and a probe molecule. The probe molecule is immobilized at the sensor element. The probe molecule associates with a receptor exposed at a surface of a detection target. The sensor element detects cleavage of the receptor having associated with the probe molecule.

21 Claims, 16 Drawing Sheets

(56) References Cited

U.S. PATENT DOCUMENTS

| | | | |
|---|---|---|---|
| 2015/0148265 A1* | 5/2015 | Baym | A61B 5/4839 |
| | | | 506/39 |
| 2016/0313316 A1 | 10/2016 | Yao et al. | |
| 2018/0275084 A1 | 9/2018 | Saito et al. | |

FOREIGN PATENT DOCUMENTS

| | | | | |
|---|---|---|---|---|
| JP | 2006-126162 A | | 5/2006 | |
| JP | 2013-50426 | | 3/2013 | |
| JP | 2016-166900 | | 9/2016 | |
| JP | 2016-208883 A | | 12/2016 | |
| JP | 2017-121205 A | | 7/2017 | |
| JP | 2018-163146 A | | 10/2018 | |
| JP | 2018163146 A | * | 10/2018 | |
| KR | 10-2016-0085717 A | | 7/2016 | |
| WO | WO-2016111568 A1 | * | 7/2016 | G01N 21/62 |
| WO | WO 2017/126617 A1 | | 7/2017 | |

OTHER PUBLICATIONS

Artyukhin et al "Functional One-Dimensional Lipid Bilayers on Carbon Nanotube Templates" J. Am. Chem. Soc. 2005, 127, 7538-7542) (Year: 2005).*

Wicklein et al "Biomimetic Architectures for the Impedimetric Discrimination of Influenza Virus Phenotypes" Adv. Funct. Mater. 2013, 23, 254-262) (Year: 2013).*

Sun "Modifications to the Hemagglutinin Cleavage Site Control the Virulence of a Neurotropic H1N1 Influenza Virus" Journal of Virology, Sep. 2010, p. 8683-8690 (Year: 2010).*

T. Kawata et al. "Detection of Influenza Virus Using Cell Mimetic Graphene FET", The 78$^{th}$ JSAP Autumn Meeting, 2017, 8a-C16-13, The Japan Society of Applied Physics, 3 pages ( with English Translation).

Andrea-Stieneke-Groeber et al., "Influenza virus hemagglutinin with multibasic cleavage site is activated by furin, a subtilisin-like endoprotease", The EMBO Journal vol. 11 No. 7, pp. 2407-2414, 1992.

Mutsuo Yamaya et al., "Activation of influenza virus by airway epithelial proteases: a potential treatment for influenza", Annals of The Japanese Respiratory Society, 5(4), 2016, 25 pages ( with English translation).

* cited by examiner

|  | BIRD-INFECTING INFLUENZA (IMPLANTS IN α-2,3-SUGAR CHAIN (BIRD RESPIRATORY TRACT CELL)) | HUMAN-INFECTING INFLUENZA (IMPLANTS IN α-2,6-SUGAR CHAIN (HUMAN RESPIRATORY TRACT CELL)) |
|---|---|---|
| WEAK VIRULENCE (INFECTS RESPIRATORY TRACT) | ALREADY EXISTS LOW PATHOGENIC AVIAN INFLUENZA (LPAI) | ALREADY EXISTS |
| STRONG VIRULENCE (INFECTS ORGANS OF ENTIRE BODY) | ALREADY EXISTS HIGHLY PATHOGENIC AVIAN INFLUENZA (HPAI) | NOT YET EXIST POTENTIAL THREAT CAUSING CATASTROPHY |

HUMAN-TYPE RECEPTOR

BIRD-TYPE RECEPTOR

DETECTION DEVICE AND DETECTION METHOD

CROSS-REFERENCE TO RELATED APPLICATION

This application is based upon and claims the benefit of priority from Japanese Patent Application No. 2017-221876, filed on Nov. 17, 2017; the entire contents of which are incorporated herein by reference.

FIELD

Embodiments described herein relate generally to a detection device and a detection method.

BACKGROUND

Among influenza virus A, avian influenza is typified by, for example, type A subtype H5N1, infects organs of the entire body, has a high fatality rate, and is therefore called strongly virulent. Currently, there have been no pandemics of type A subtype H5N1 because humans are not infected easily; but in the case where novel influenza that infects humans occurs due to a mutation, the occurrence of devastating harm is predicted.

On the other hand, the rapid testing of influenza is practical using immunochromatography, etc.; but rapid testing technology to identify strong virulence and weak virulence has not yet been established; and currently, it is necessary to perform genetic testing after gene amplification by PCR (Polymerase Chain Reaction). If novel influenza undesirably occurs, it is predicted that infection will spread rapidly; therefore, it is predicted that it will be difficult to suppress the spread of the infection without a rapid testing method.

A method in which a virus is captured by using a probe molecule binding to a marker of the virus surface is known as technology for specifically detecting the virus; but this method is problematic in that it is difficult to increase the sensitivity because it is difficult to identify cases where a contaminant nonspecifically adsorbs to the probe molecule or to portions other than the probe molecule. It is also problematic in that identification cannot be performed in the case where viruses have surface markers that bind to the same probe molecule.

BRIEF DESCRIPTION OF THE DRAWINGS

FIG. 1 is a drawing showing a structure of influenza virus A;

FIG. 2 is a figure showing classifications of influenza A;

DETAILED DESCRIPTION

Figure 3:
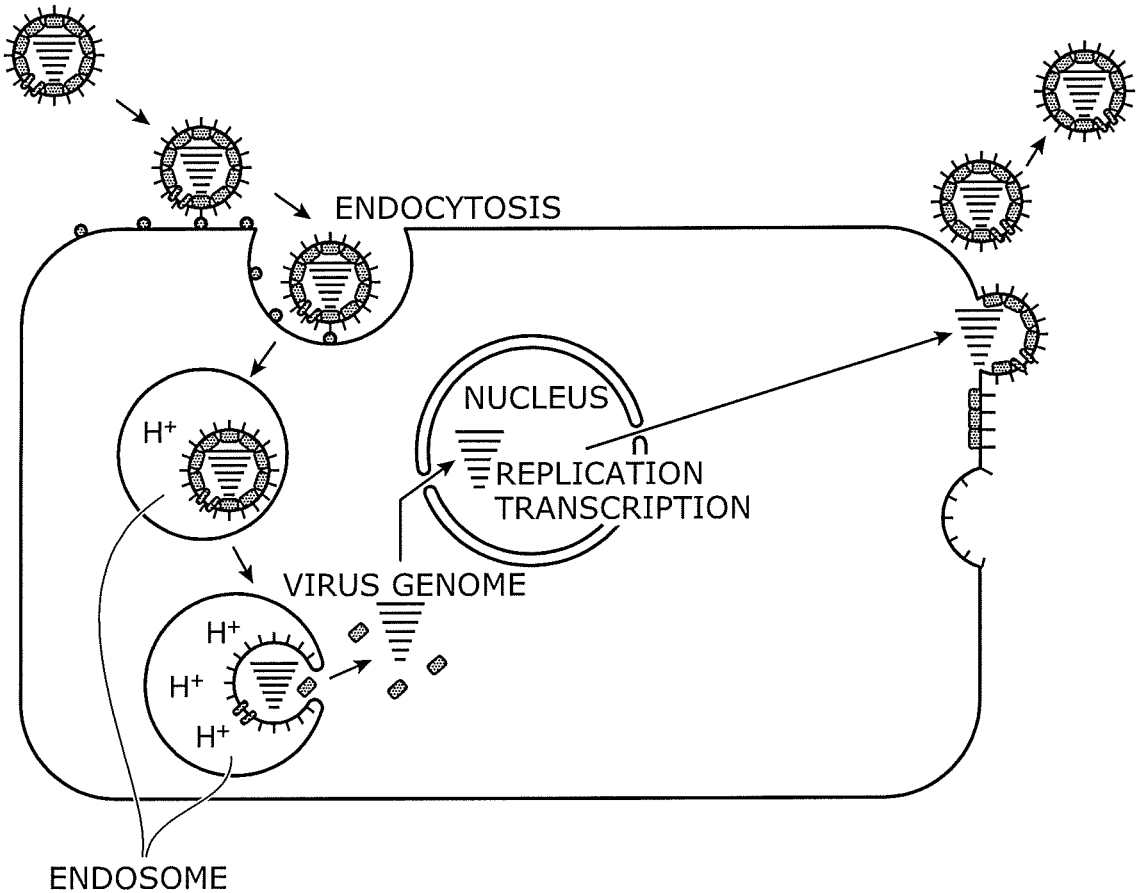
FIG. 3 is a drawing showing an infection mechanism of an influenza virus.

According to one embodiment, a detection device includes a sensor element and a probe molecule. The probe molecule is immobilized at the sensor element. The probe molecule associates with a receptor exposed at a surface of a detection target. The sensor element detects cleavage of the receptor having associated with the probe molecule.

Hereinafter, embodiments will be described with reference to the drawings. Incidentally, in the respective drawings, the same components are denoted by the same reference numerals.

According to embodiments described below, a detection device and a detection method are provided that detect a virus as a detection target. In particular, the detection device and the detection method are provided in which identification between strong virulence and weak virulence is performed rapidly for an influenza virus; identification between bird-infecting and human-infecting types is performed rapidly; and a human-infecting strongly-virulent influenza virus that has not yet appeared can be detected specifically.

FIG. 1 is a drawing showing the structure of influenza virus A.

The influenza virus is a vesicle having a diameter of about 100 nm that is wrapped in a lipid bilayer (a surface membrane) called an envelope 31 and has a single-strand of RNA (ribonucleic acid) as a genome in the interior of the envelope 31. Spike proteins (proteins sticking into the membrane) called hemagglutinin (HA) and neuraminidase (NA) are exposed at the surface of the envelope 31. In the following description, hemagglutinin also may be called HA; and neuraminidase also may be called NA.

The influenza virus has the types of type A, type B, and type C. Type C infects infants; but the pathogenicity is low; and symptoms often do not appear. Also, type C infects only humans. Epidemics of type B repeat each year; the gene is stable; immunity to the virus may be maintained a long time; and the scale of epidemics is small. Type B also infects only humans. Influenza A has many mutant types; and global large-scale epidemics occur easily. There are types of type A that infect organisms other than humans.

Type A and type B include HA and NA, and have no large structural differences. Type C does not include HA and NA; instead, hemagglutinin-esterase (HE) is expressed.

FIG. 2 is a figure showing classifications of influenza A.

FIG. 3 is a drawing showing the infection mechanism of the influenza virus.

Figure 4A:
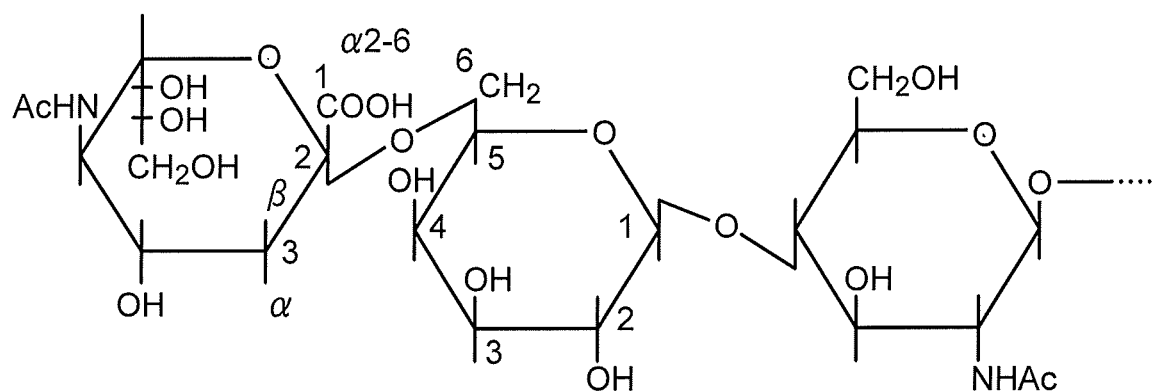
FIG. 4A is a drawing showing a molecular structure of a sugar chain expressed in an upper respiratory tract of a human.
Figure 4B:
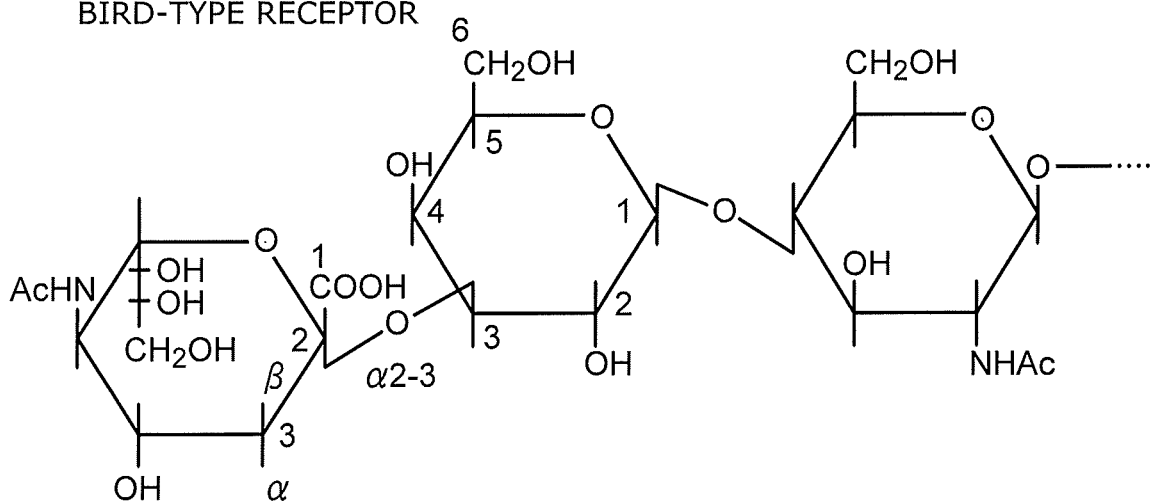
FIG. 4B is a drawing showing a molecular structure of a sugar chain expressed in an upper respiratory tract of a bird.

FIG. 4A is a drawing showing the molecular structure of a sugar chain expressed in the upper respiratory tract of a human; and FIG. 4B is a drawing showing the molecular structure of a sugar chain expressed in the upper respiratory tract of a bird.

Influenza virus A has types that infect birds and types that infect humans. This is because the molecular structure is different between birds and humans for the sugar chains expressed in the cells of the upper respiratory tract where the influenza initially adsorbs when infecting. When the influenza virus adsorbs to the cell, the HA that is exposed at the virus surface recognizes and binds to a sugar chain exposed at the cell membrane surface.

As shown in FIG. 4B, the sugar chain that is exposed in the upper respiratory tract of a bird has an α-2,3-structure; and as shown in FIG. 4A, the sugar chain that is exposed in the upper respiratory tract of a human has an α-2,6-structure. The difference is due to the bonding carbon positions of the galactose and the sialic acid at the sugar chain end.

Birds are infected by a virus in which HA binding specifically to the α-2,3-sugar chain is expressed; and humans are infected by a virus in which HA binding specifically to the α-2,6-sugar chain is expressed. HA is a receptor or a sugar chain recognition site.

As shown in FIG. 2, influenza A mainly includes weakly-virulent influenza of which infection spreads only to the respiratory tract, and strongly-virulent influenza of which infection spreads to organs of the entire body. The Spanish flu and the swine influenza epidemic of North and Central America in 2009 that produced many victims in the past are classified as weakly virulent which is the same as seasonal influenza. On the other hand, avian influenza such as subtype H5N1, which is feared enough to be called the fowl plague, is classified as strongly virulent.

As shown in FIG. 3, the influenza virus adsorbs to the cell of the host by the HA recognizing and binding to a sugar chain. Subsequently, the influenza virus is engulfed by the cell by the devouring action of the cell called endocytosis.

The influenza virus is enclosed inside a vesicle called an endosome by the endocytosis. The HA is cleaved by a protease inside the endosome. By the interior of the endosome becoming acidic, the three-dimensional structure of the cleaved HA molecule changes; the envelope 31 of the virus fuses with the endosomal membrane; and genomes of the virus are released into the cell.

Figure 5A:
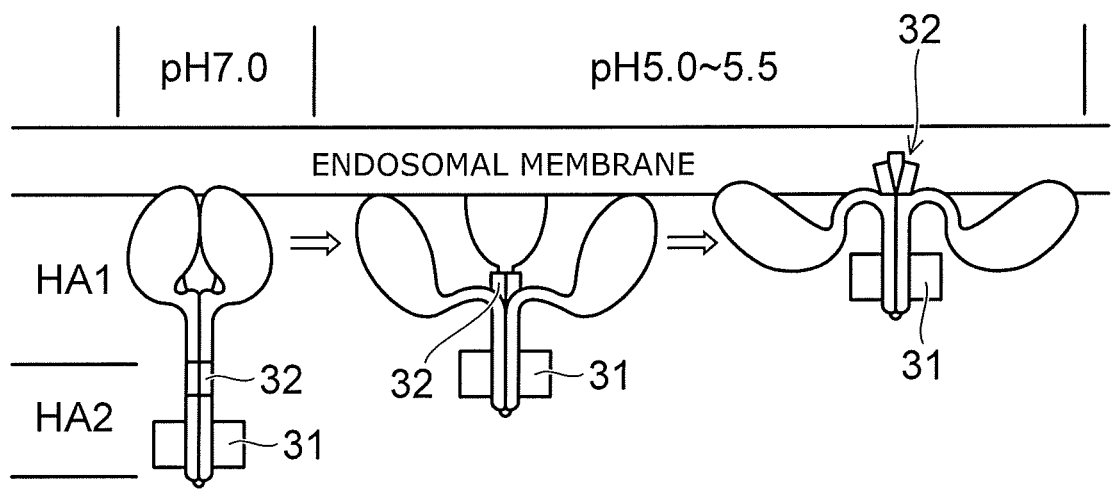
FIGS. 5A and 5B are schematic views showing a deformation of a cleaved hemagglutinin (HA) due to pH.
Figure 5B:
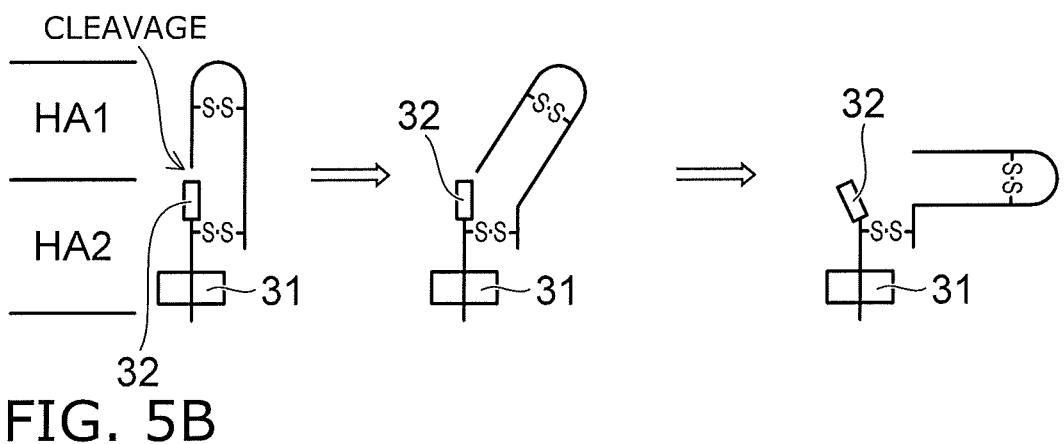

FIGS. 5A and 5B are schematic views showing the deformation of the cleaved HA due to pH.

HA forms a trimer as shown in FIG. 5A. FIG. 5B is a drawing in which one HA is extracted.

The alteration of HA starts by a designated site being cut (cleaved) by a protease (a proteolytic enzyme) existing inside the endosome. The cleaved HA is broken into HA1 that binds to a sugar chain on the endosomal membrane side, and HA2 that is immobilized at the envelope 31 of the virus.

On the other hand, the interior of the endosome becomes acidic due to proton pumps that extend through the endosomal membrane and pump protons.

When the interior of the endosome becomes weakly acidic (pH 5.0 to 5.5), the cleaved HA deforms; and a hydrophobic group 32 at the cleaved portion protrudes.

Figure 6:
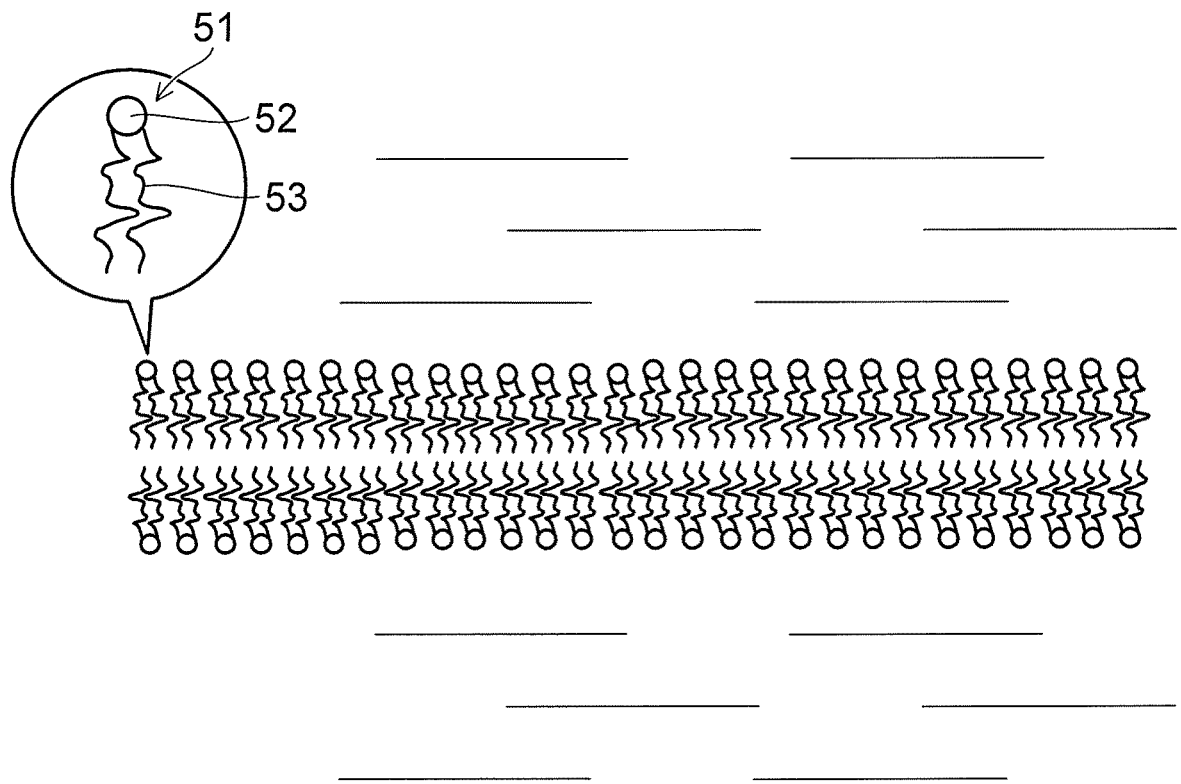
FIG. 6 is a schematic view showing a general structure of a lipid bilayer.

FIG. 6 is a schematic view showing a general structure of the lipid bilayer.

The lipid bilayer is made from a phospholipid molecule 51 in which a hydrophilic phosphate group (hydrophilic group) 52 and a hydrophobic long-chain fatty acid (hydrophobic group) 53 bind. In many cases, two fatty acids 53 bind to one phosphate group 52. In an aqueous solution such as a biological liquid, there is a tendency for the hydrophilic group 52 to be exposed at the surface (the aqueous solution side), and for the fatty acids 53 (the hydrophobic groups) to coalesce together. Here, in the case where there is only one hydrophobic fatty acid 53, a spherical micelle structure is formed in which the hydrophilic phosphate groups 52 face outward; but in the case where there are two fatty acids 53, the enclosure in a micellar structure is not possible because the diameters of the phosphate group 52 and the fatty acid 53 are similar; and a structure is formed in which two molecules are arranged in a layer configuration so that the fatty acids 53 face each other. This is the lipid bilayer.

The endosomal membrane that engulfs the virus, the cell membrane infected by the virus, and the viral membrane (the envelope) 31 described above each have the structure of the lipid bilayer recited above.

Thus, the greater part of the lipid bilayer forming the endosomal membrane other than the phosphate groups 52 at the front and back surfaces is formed of the hydrophobic fatty acid 53; therefore, as shown in FIG. 5A, the hydrophobic group 32 that protrudes due to the cleavage of the HA can stick into the endosomal membrane due to a hydrophobic interaction. This causes membrane fusion of the endosomal membrane and the envelope 31 of the virus.

The cleaving of the HA occurs due to the protease (the proteolytic enzyme). The protease recognizes and cuts the amino acid sequence of the protein. The virus itself does not have such a protease, and utilizes a protease of the infected cell or of the periphery of the infected cell.

A protease called trypsin exists in the respiratory tract of a human; and HA that is cleaved by trypsin is expressed in human-infecting influenza viruses.

TMPRSS (transmembrane protease/serine) 2 which is type-II transmembrane serine protease also is expressed at the cell surface of the human respiratory tract; and HA of human-infecting influenza viruses also is cleaved by TMPRSS2.

However, these proteases rarely exist in human organs other than the respiratory tract; therefore, currently, the infection of human-infecting influenza viruses spreads only to the respiratory organs; and an infection spreading to organs of the entire body is rare.

For example, a protease called furin exists in organs of the entire body. Furin is a protease that exists in large amounts in Golgi bodies which are organelle of a cell.

HA that has an amino acid sequence that is cleaved by furin is expressed in bird-infecting influenza viruses such as subtype H5N1, etc.

Because furin exists in the entire body, if an infection of the types of influenza recited above occurs, the infection undesirably spreads to organs of the entire body, causing serious symptoms. This is why such infections are feared enough to be called the fowl plague or strongly-virulent influenza.

Strongly-virulent influenza includes a strongly-virulent influenza in which the HA is not cleaved by furin but is cleaved by a protease called TMPRSS13/MSPL.

As recited above, the difference between the bird-infecting type and the human-infecting type is caused by the difference between the structures of the sugar chains to which the HA recognizes/binds; and the difference between weak virulence and strong virulence is caused by the difference between the proteases cleaved by HA.

Currently, it is considered that a human-infecting strongly-virulent influenza virus has not yet appeared. However, both bird-infecting viruses and human-infecting viruses can infect pigs; therefore, it is pointed out that there is a risk that a hybrid-type of a bird-infecting type and a human-infecting type may be produced inside the body of a pig infected with the two viruses.

Considering the description recited above, the embodiments of the invention provide a detection device and a detection method that rapidly and specifically detect human-infecting strongly-virulent influenza that threatens to cause a pandemic.

The embodiments of the invention can specifically detect a human-infecting strongly-virulent influenza virus by utilizing the characteristic of the influenza virus recognizing and binding to a designated sugar chain structure by the HA exposed at the surface, and by the characteristic of the HA being cleaved by a designated protease.

According to the embodiments of the invention, it is possible to specifically detect all four types classified by the two characteristics of infection type and virulence shown in FIG. 2.

The detection target is not limited to an influenza virus; and it is possible to detect anything having the characteristic of a receptor exposed at the surface recognizing/binding to a designated target and the receptor being cleaved by a protease.

Figure 7:
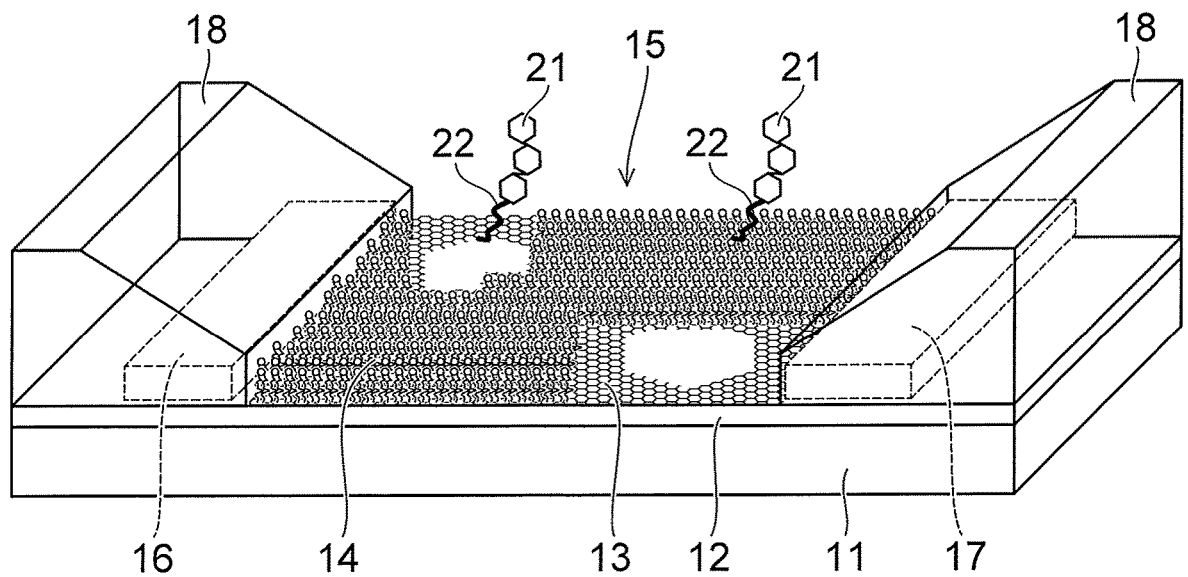
FIG. 7 is a schematic view showing an overview of a detection device of an embodiment.

FIG. 7 is a schematic view showing an overview of the detection device (a biosensor) of the embodiment.

Figure 8:
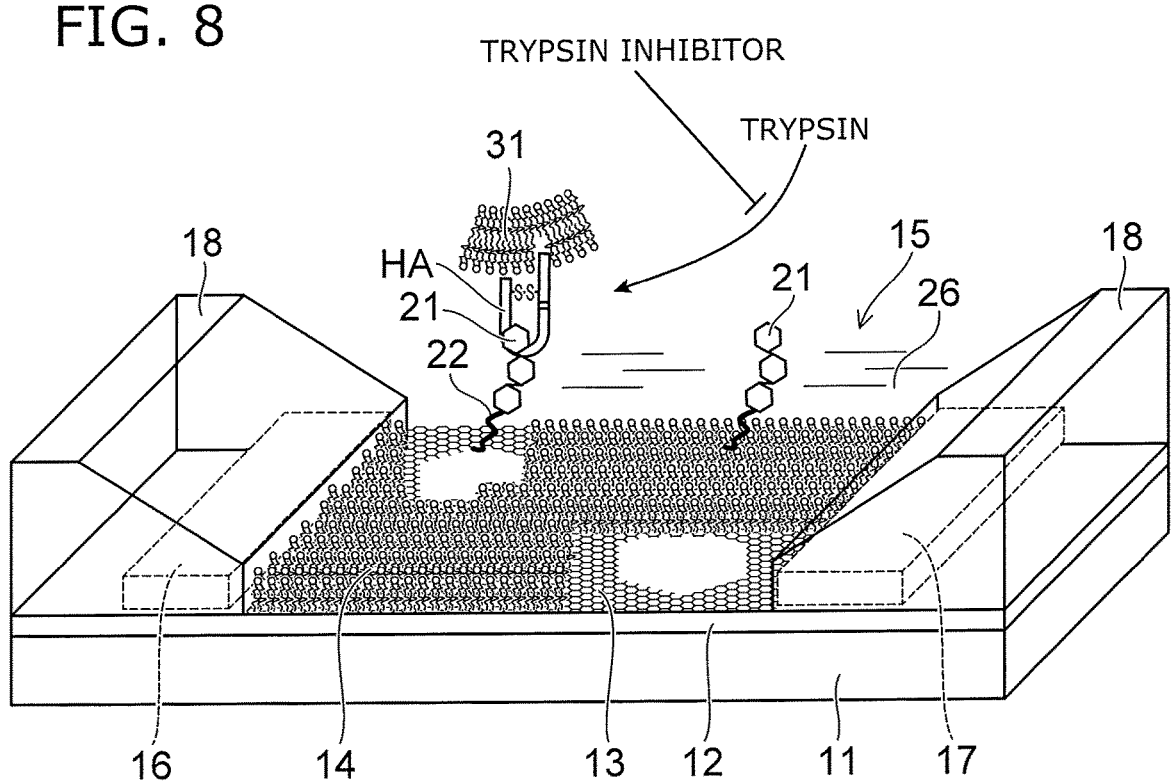
FIG. 8 is a schematic view showing a state in which a human-infecting influenza virus is captured using the detection device of the embodiment.

FIG. 8 is a schematic view showing the state in which a human-infecting influenza virus is captured using the detection device of the embodiment.

Figure 9:
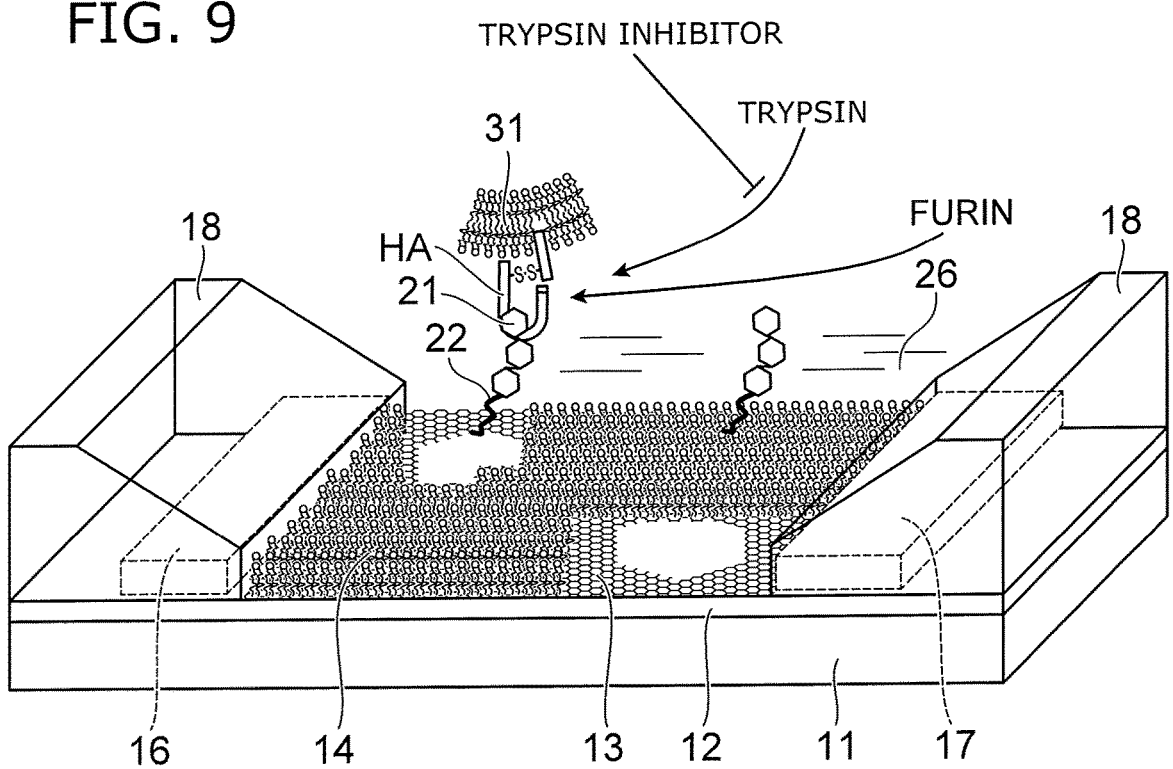
FIG. 9 is a schematic view showing a state in which a strongly-virulent influenza virus is detected using the detection device of the embodiment.

FIG. 9 is a schematic view showing the state in which a strongly-virulent influenza virus is detected using the detection device of the embodiment.

Figure 10:
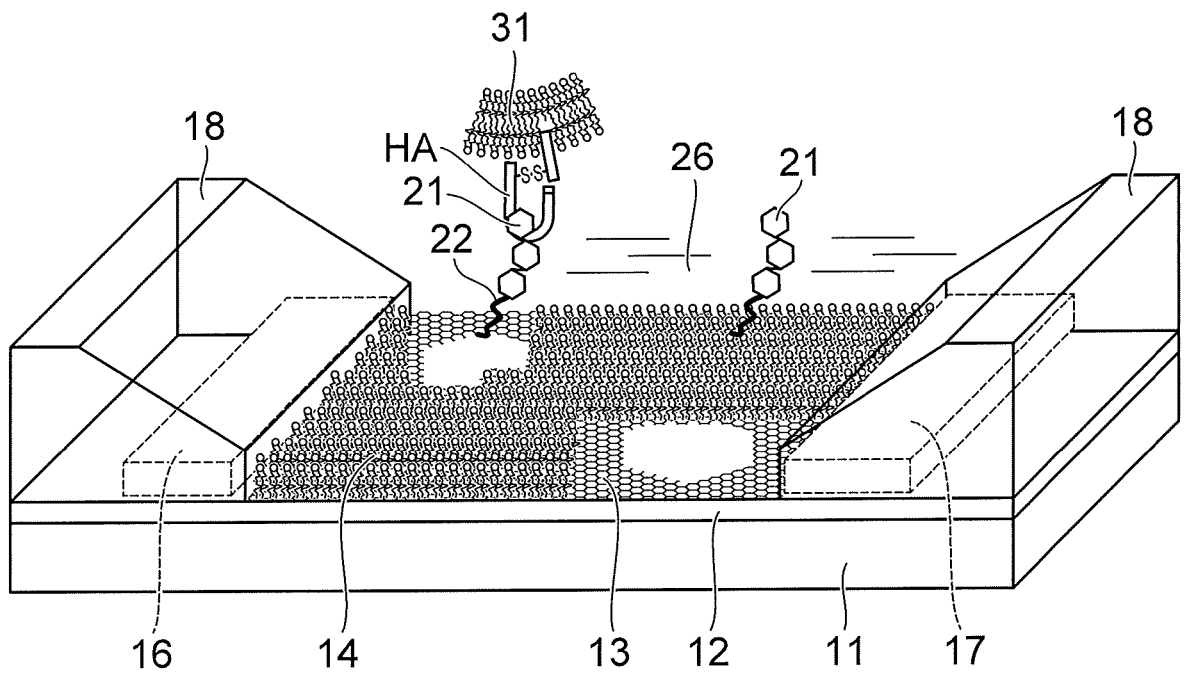
FIG. 10 is a schematic view showing a state in which a cleaving of a HA of a virus is detected using the detection device of the embodiment.

FIG. 10 is a schematic view showing the state in which the cleaving of the HA of the virus is detected using the detection device of the embodiment.

Figure 11:
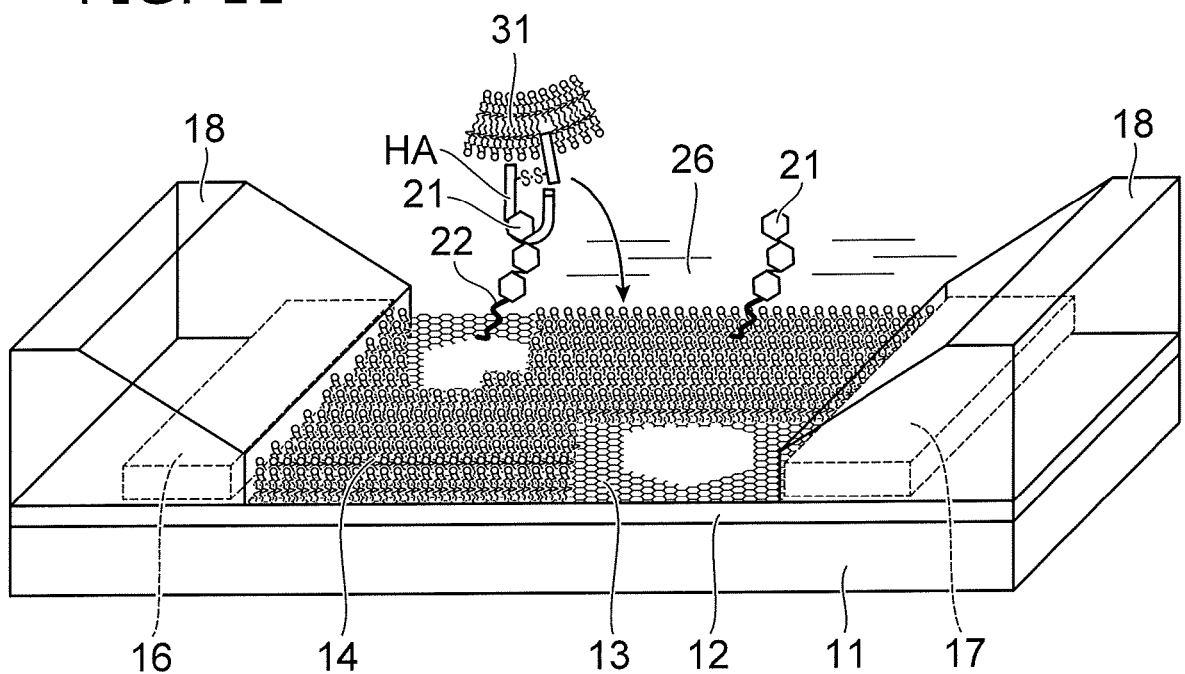
FIG. 11 is a schematic view showing a state in which a membrane fusion after the cleaving of the HA of the virus is detected using the detection device of the embodiment.

FIG. 11 is a schematic view showing the state in which the membrane fusion after the cleaving of the HA of the virus is detected using the detection device of the embodiment.

As shown in FIG. 7, the detection device of the embodiment includes a sensor element, and a probe molecule 21 immobilized at the sensor element. The sensor element is, for example, a charge detection element including a graphene film 13. The probe molecule 21 is an α-2,6-sugar chain and associates with the HA exposed at the surface of the influenza virus.

A foundation film 12 is provided on a substrate 11; and the graphene film 13 is provided on the foundation film 12. Or, the graphene film 13 may be provided on the surface of the substrate 11 without providing the foundation film 12. Not-illustrated circuits and/or transistors may be formed in the substrate 11.

For example, silicon, silicon oxide, glass, or a polymer material may be used as the material of the substrate 11. The foundation film 12 is, for example, an insulating film such as a silicon oxide film or a fluorocarbon resin. The foundation film 12 also may have the function of a chemical catalyst for forming the graphene film 13.

A phospholipid film 14 (a phospholipid monolayer film) covers the graphene film 13; and the probe molecule 21 is immobilized at one of the graphene film 13 or the phospholipid film 14 (the phospholipid monolayer film) via a linker 22. The linker 22 adjusts the distance between the probe molecule 21 and the surface of the sensor element.

For easier the understanding of the internal structure, a portion of the phospholipid film 14 (the phospholipid monolayer film) is intentionally not illustrated so that the graphene film 13 of the foundation can be seen in several drawings including FIG. 7 to FIG. 11. Although the probe molecule 21 is illustrated in the state in which three monosaccharides are bound, the number is not limited thereto.

For example, the sensor element has an FET (field effect transistor) structure and includes at least two electrodes (a first electrode 16 and a second electrode 17). The graphene film 13 is electrically connected to the first electrode 16 and the second electrode 17. One of the first electrode 16 or the second electrode 17 functions as a drain electrode; and the other functions as a source electrode. A current can be caused to flow between the first electrode 16 and the second electrode 17 via the graphene film 13.

The graphene film 13, the phospholipid film 14 (the phospholipid monolayer film), and the probe molecule 21 are disposed in a well surrounded with a sidewall 18. An inlet opening 15 that supplies a specimen liquid or the like is formed above the well.

When a specimen liquid (e.g., a throat swab liquid, gargled water, or the like) that is acquired from a subject is dropped into the well, in the case where the subject is infected with human-infecting influenza, the HA of the influenza virus recognizes the probe molecule (the α-2,6-sugar chain) 21 and binds to the probe molecule (the α-2,6-sugar chain) 21 as shown in FIG. 8.

The case is similar where spray scattering in air due to a cough is captured. In the case where the spray of the cough of a person infected with human-infecting influenza is included in the captured spray, the HA of the influenza virus binds to the probe molecule (the α-2,6-sugar chain) as shown in FIG. 8.

The virus that is captured by the sugar chain becomes proximal to the graphene film 13. Generally, an influenza virus has a surface charge; therefore, when the charge of the virus becomes proximal to the graphene film 13, the potential of the graphene fluctuates; and the source-drain current that flows through the graphene film 13 fluctuates. Accordingly, the existence or absence of a human-infecting influenza virus can be determined by reading the fluctuation of the source-drain current.

In the case where a protease that exists in organs of the entire body and cleaves the HA of a strongly-virulent influenza virus is supplied to the well, the HA that is bound to the α-2,6-sugar chain is cleaved as shown in FIG. 9 if the influenza virus that is captured by the probe molecule (the α-2,6-sugar chain) 21 is strongly virulent.

When the HA is cleaved, the immobilization of the virus with respect to the sensor element becomes unstable as shown in FIG. 10; and it is possible to detect this instability as a fluctuation of an electrical characteristic.

Or, if a specimen liquid 26 is caused to be acidic, the cleaved HA deforms as shown in FIG. 11; and the hydrophobic group of the HA sticks into the phospholipid film 14 (the phospholipid monolayer film) covering the surface of the graphene film 13. The cleaving of the HA can be detected with high sensitivity by detecting the fluctuation of an electrical characteristic of the sensor element due to this event. Subsequently, the cleaving of the HA can be detected with high sensitivity by detecting the fluctuation of an electrical characteristic of the sensor element due to the envelope 31 of the virus fusing with the phospholipid film 14 (the phospholipid monolayer film).

Here, for example, an acidic buffer solution such as acetate-NaOH may be used as a pH adjusting liquid to cause the specimen liquid 26 to be acidic to cause the HA to deform.

For example, furin may be used as the protease that exists in organs of the entire body and cleaves the HA of the strongly-virulent influenza virus.

Or, by using TMPRSS13/MSPL which is known to cleave the HA of strongly-virulent bird-infecting influenza, a novel influenza virus can be detected in the case where the novel influenza virus appears due to this type of bird-infecting strongly-virulent influenza mutating into a human-infecting type. Because TMPRSS13/MSPL is one type of transmembrane serine protease, it is also possible to pre-immobilize TMPRSS13/MSPL at the phospholipid film 14 (the phospholipid monolayer film) covering the surface of the graphene film 13.

Any throat swab liquid or spray due to a cough that is used as the specimen is from the upper respiratory tract of a human and therefore may include trypsin.

In the case where a sufficient amount of trypsin is included in the specimen liquid, the HA is undesirably cleaved even for a weakly-virulent influenza virus; therefore, a false positive indicating a strongly-virulent influenza virus undesirably occurs.

For example, it is possible to supply a trypsin inhibitor to the well as a method for avoiding this risk.

In the case where the trypsin inhibitor specifically obstructs the enzyme activity of trypsin and does not affect the enzyme activity of furin and/or TMPRSS13/MSPL, the trypsin inhibitor may be supplied as shown in FIG. 9; and by further supplying, for example, furin, a strongly-virulent influenza virus can be detected if the HA is cleaved.

By using the methods recited above, if it is detected that the virus is immobilized at the probe molecule (the α-2,6-sugar chain) 21 and it is confirmed that the virus is cleaved by one of furin or TMPRSS13/MSPL, the virus can be determined to be human-infecting strongly-virulent influenza, i.e., an exceedingly dangerous novel influenza.

In the case where the trypsin inhibitor undesirably obstructs the enzyme activity of furin and/or TMPRSS13/MSPL, it is possible to detect the cleaving behavior of the HA by supplying the trypsin inhibitor and immobilizing the human-infecting influenza virus at the probe molecule (the α-2,6-sugar chain) 21 as shown in FIG. 8, subsequently removing the trypsin inhibitor and the trypsin from the well by cleaning, and by subsequently supplying furin and/or TMPRSS13/MSPL to the well.

By using the methods recited above, the virus can be determined to be human-infecting weakly-virulent influenza, i.e., seasonal influenza, in the case where the virus is detected to be immobilized at the probe molecule (the α-2,6-sugar chain) 21, but cleaving by either furin or TMPRSS13/MSPL is not confirmed.

This is determined more reliably by further supplying trypsin. By supplying trypsin, human-infecting weakly-virulent influenza can be confirmed if the cleaving of the HA is confirmed.

Or, it is also possible to determine the virulence by preparing two sensor elements of a first sensor element in which furin and TMPRSS13/MSPL are supplied to the well, and a second sensor element in which trypsin is supplied to the well, by supplying the specimen liquid to the two, and by determining the virulence using each sensor element. For example, the well of the first sensor element and the well of the second sensor element are separated by the sidewall 18.

If the result of the first sensor element is positive, the detected virus is human-infecting strongly-virulent influenza; and if the result of the first sensor element is negative and the result of the second sensor element is positive, the detected virus is human-infecting weakly-virulent influenza.

However, if the results of both the first sensor element and the second sensor element are negative, the existence of bird-infecting influenza cannot be negated.

Therefore, by performing the methods recited above using an α-2,3-sugar chain as the probe molecule 21, bird-infecting strongly-virulent influenza and weakly-virulent influenza can be detected specifically similarly to the description recited above.

An element (a region) capable of detecting a human-infecting influenza virus in which an α-2,6-sugar chain is immobilized on the sensor element as the probe molecule 21 may coexist inside the same well with an element (a region) capable of detecting a bird-infecting influenza virus in which an α-2,3-sugar chain is immobilized on the sensor element as the probe molecule 21.

Reagents such as the protease for cleaving HA, the protease inhibitor for obstructing the nonspecific cleaving of HA, the pH adjusting liquid for promoting the membrane fusing after the cleaving of the HA, etc., described above may be supplied to the well via the injection opening 15 similarly to the specimen liquid. Or, the reagents may be placed in a liquid reservoir formed separately from the well on the substrate 11 and supplied to the well from the liquid reservoir.

Also, a unit may be provided that receives a detection signal after the sensor element detects the association between the virus and the probe molecule and automatically supplies the reagents recited above to the well.

Figure 12:
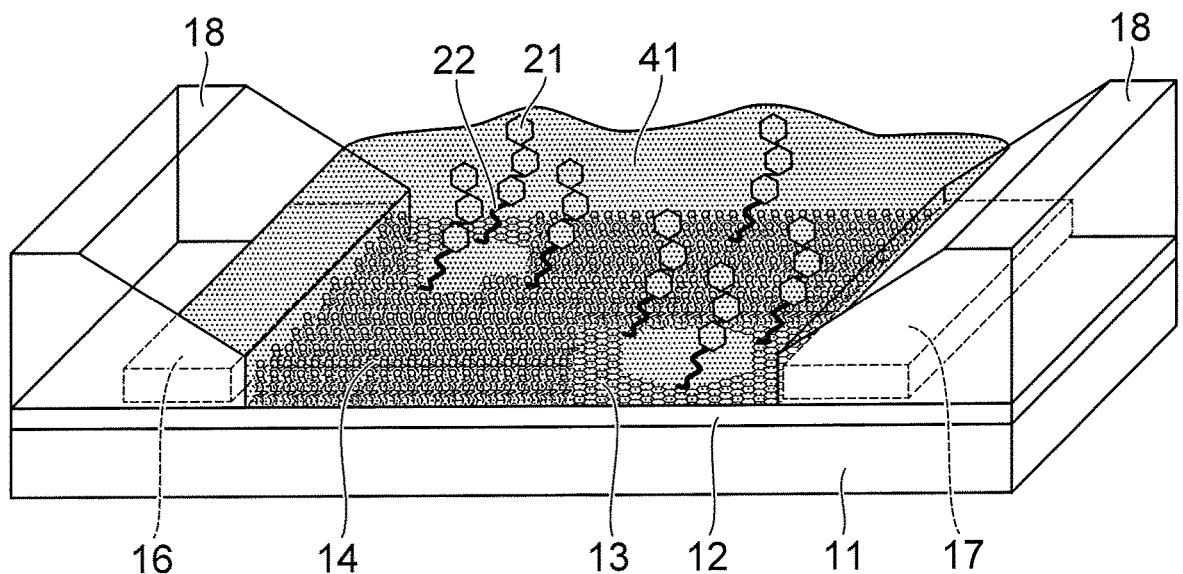
FIG. 12 is a schematic view showing a structure in which reagents are provided on a sensor element by using a hydrogel.

FIG. 12 is a schematic view showing a structure in which the reagents recited above are provided on the sensor element by using a hydrogel.

Thus, the reagents recited above also can be immobilized as a covering on the sensor element as a water-soluble hydrogel 41.

Figure 13:
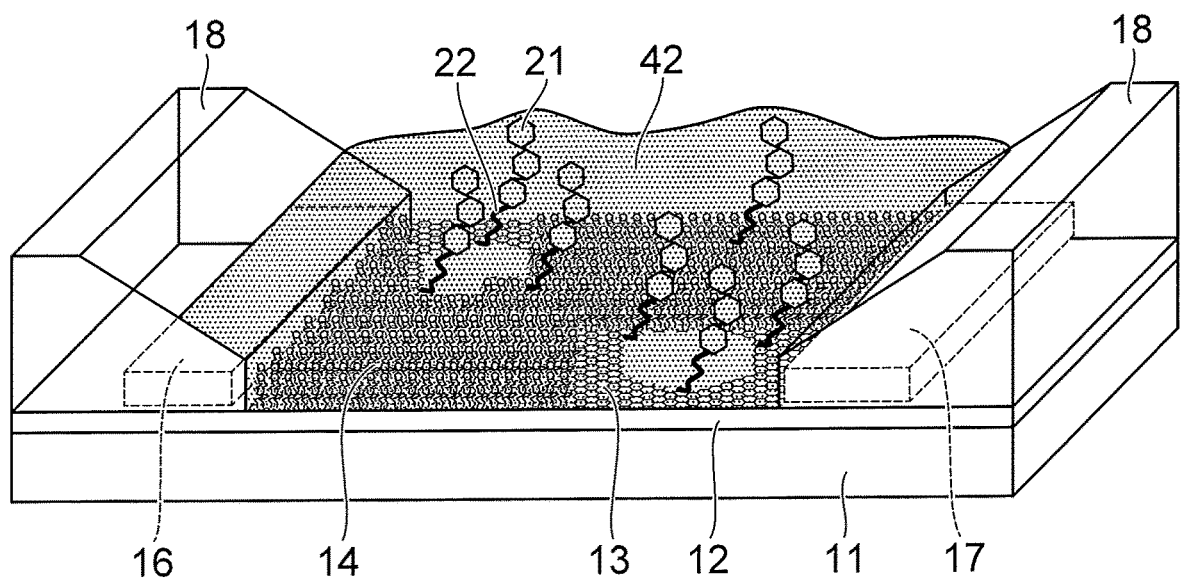
FIG. 13 is a schematic view showing a structure in which reagents are immobilized on a sensor element with an ionic liquid.

FIG. 13 is a schematic view showing a structure in which the reagents recited above are dispersed in an ionic liquid (or a high viscosity liquid) on the sensor element.

Thus, it is also possible to disperse the reagents recited above in the hydrophilic ionic liquid 42 on the sensor element.

FIGS. 14A to 14H are drawings showing molecular structures of examples of the ionic liquid 42.

Figure 14A:
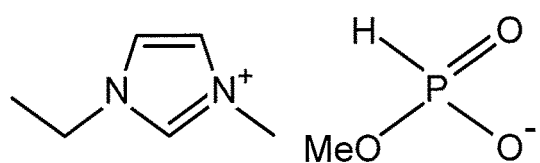
FIGS. 14A to 14H are drawings showing molecular structures of examples of an ionic liquid.
Figure 14B:
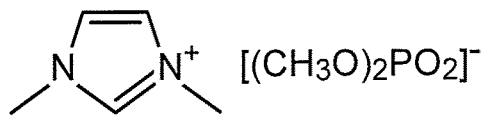
Figure 14C:
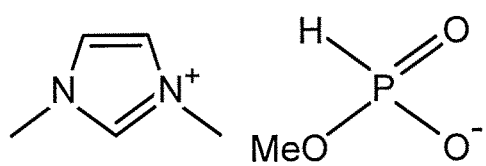
Figure 14D:
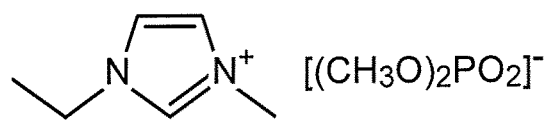
Figure 14E:
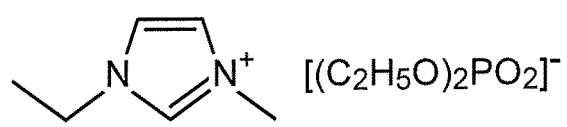
Figure 14F:
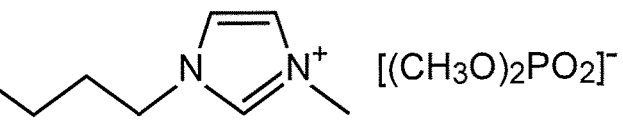
Figure 14G:
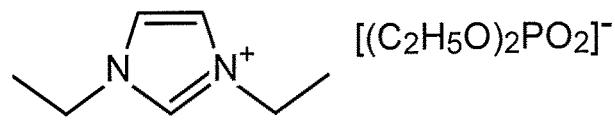
Figure 14H:
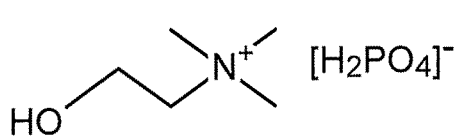

For example, a substance made of an imidazolium-based cation and a phosphonate-based anion such as that shown in FIG. 14A may be used as the ionic liquid 42. This type of ionic liquid is benign for biological materials and can markedly avoid damage to the sugar chain, the phospholipid film, etc.

Because various molecular structures of the ionic liquid can be selected, for example, it is easy to immobilize the ionic liquid with the reagent on the sensor element if the ionic liquid has a large molecular size and the viscosity is high. Examples of the ionic liquid in which the molecular structure is changed are shown in FIGS. 14B to 14H.

Figure 15:
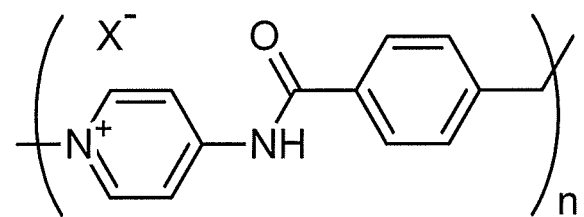
FIG. 15 is a schematic view showing a molecular structure of an organic oligomer electrolyte.

FIG. 15 is a schematic view showing the molecular structure of an organic oligomer electrolyte.

For example, it is also possible to increase the viscosity of the ionic liquid 42 by adding an organic oligomer electrolyte such as that shown in FIG. 15 as a gelling agent to the ionic liquid 42.

The hydrogel and the hydrophilic ionic liquid shown recited above each are diluted and the viscosities are reduced when the specimen liquid is supplied.

The hydrogel and the hydrophilic ionic liquid also provide the effect of maintaining a wet environment for the sugar chain probe molecule 21 and the phospholipid film 14 which are biological materials formed on the sensor element.

Figure 16:
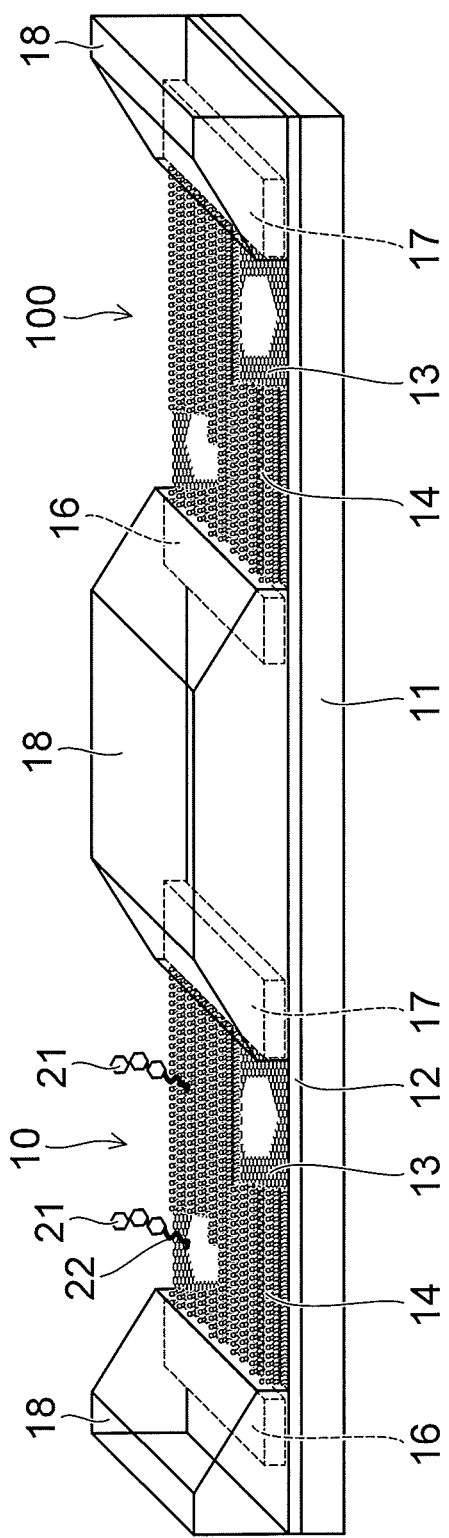
FIG. 16 is a schematic view of another example of the sensor element according to the embodiment.

FIG. 16 is a schematic view of another example of the sensor element according to the embodiment.

The sensor element shown in FIG. 16 includes a target detection element 10 in which the probe molecule 21 recited above is immobilized, and a reference element 100 in which the probe molecule is not immobilized.

The target detection element 10 and the reference element 100 are formed on the same substrate 11. The reference element 100 in which the probe molecule is not immobilized is formed at the side of the target detection element 10 in which the probe molecule 21 is immobilized.

Although a signal due to a virus is not detected in the reference element 100 in which the probe molecule is not immobilized, a fluctuation due to an external disturbance, e.g., a pH change, or the like is detected; therefore, the reference element 100 can be used to correct external disturbance noise for the target detection element 10. Although FIG. 16 illustrates a configuration in which the target detection element 10 and the reference element 100 are formed inside separate wells, the target detection element 10 and the reference element 100 may coexist inside the same well.

According to the embodiments of the invention, it is possible to detect not only an influenza virus but any substance having the characteristic of a receptor exposed at the surface and recognizing/binding to a designated target, and the receptor being cleaved by a protease.

Actually, it is known that many enveloped viruses penetrate the infected cell due to a spike protein (a protein or a sugar chain-modified protein) exposed at the surface being cleaved by a protease. For example, for HIV, the envelope glycoprotein GP160 is cleaved by furin. Also, for the SARS coronavirus, the S-protein is cleaved by trypsin.

Thus, when the spike protein is cleaved, membrane fusion of the viral envelope with the phospholipid film 14 (the phospholipid monolayer film) covering the surface of the graphene film 13 is caused. Or, the hydrophobic group that is exposed by the cleaving sticks into the phospholipid film 14.

The potential of the graphene fluctuates greatly because these changes occur at the vicinity of the graphene film 13 or in contact with the graphene film 13. In other words, a large signal is obtained from one virus; and even a low number of viruses can be detected.

The graphene film 13 is not limited to being formed on the foundation film (the insulating film) 12; and a structure may be used in which the graphene film 13 floats above the foundation.

Figure 17:
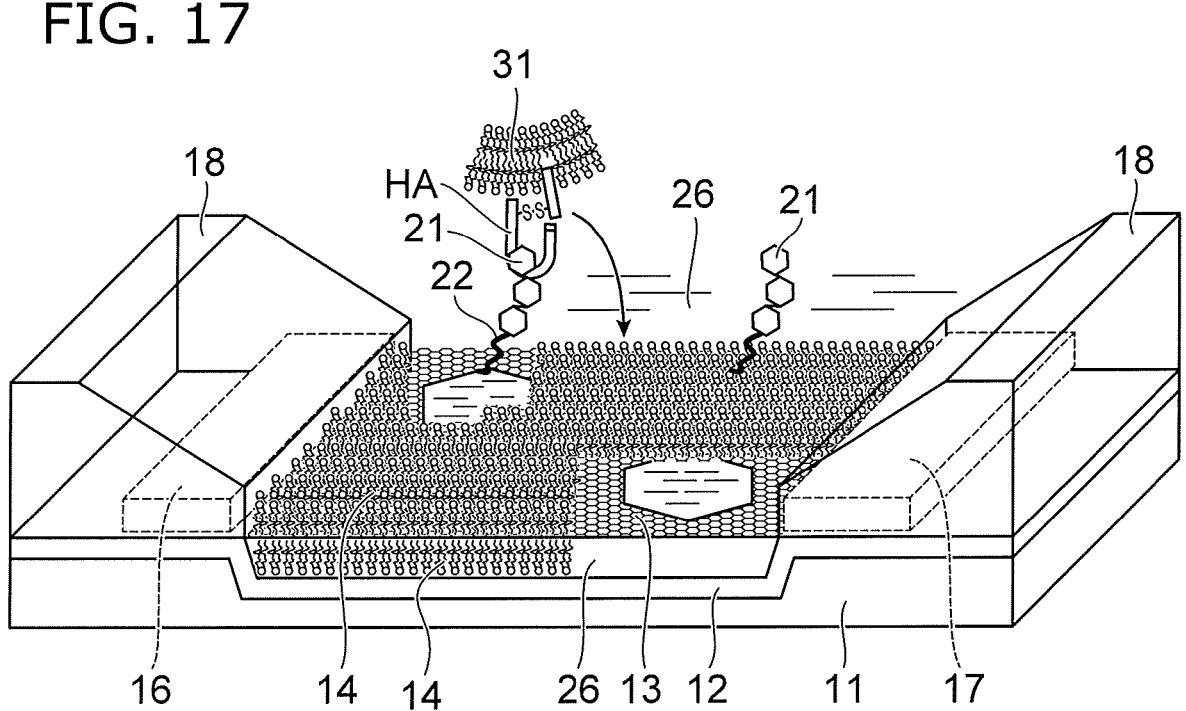
FIG. 17 is a schematic view of a detection device having a structure in which a graphene film floats above a foundation.

FIG. 17 is a schematic view of a detection device having a structure in which the graphene film 13 floats above the foundation.

Figure 18B:
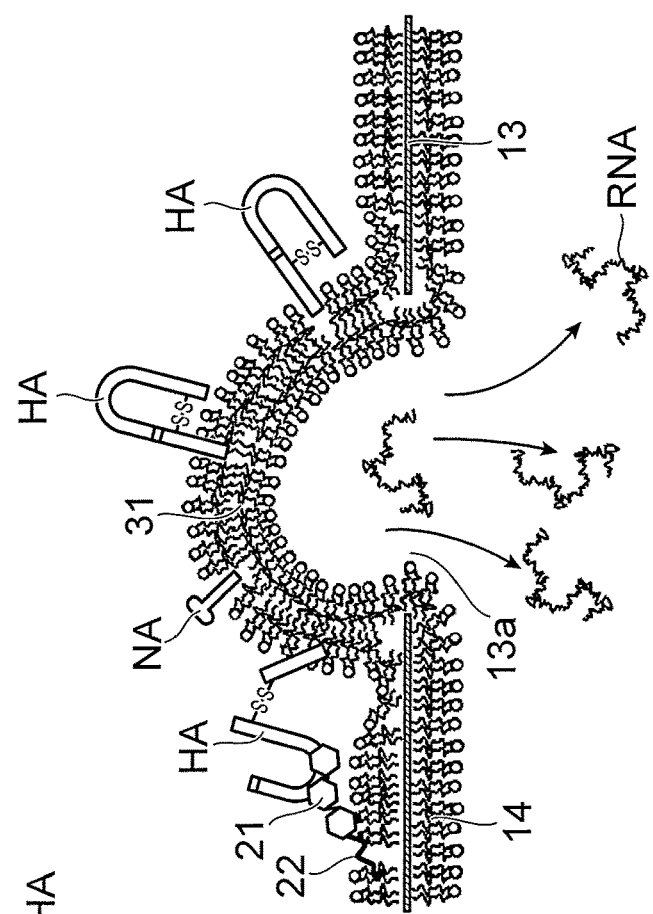
FIGS. 18A and 18B are enlarged schematic views of a vicinity of the graphene film.
Figure 18A:
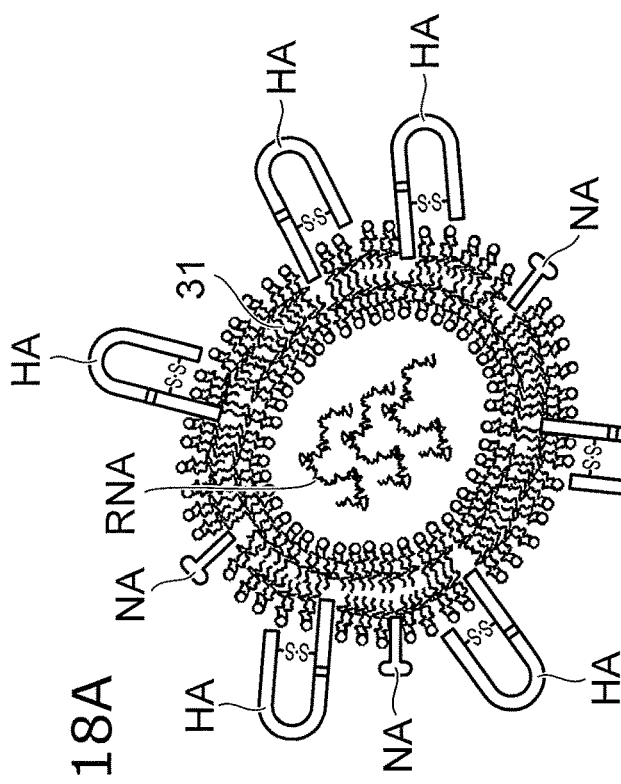

FIG. 18A is an enlarged schematic view of the vicinity of the graphene film 13.

For example, the graphene film 13 floats inside the specimen liquid 26 (the weakly acidic buffer solution) in a state like a fixed beam that is fixed by the source/drain electrodes; and the phospholipid film 14 (the phospholipid monolayer film) is formed not only on the front surface of the graphene film 13 but also on the back surface. Also, the graphene film 13 is patterned into a mesh configuration by patterning holes.

The phospholipid films 14 (the phospholipid monolayer films) at the front and back extend into the interior of a hole 13a of the graphene film 13; and a phospholipid bilayer is formed inside the hole 13a.

Here, if the cleaving of the HA by a protease and the deformation of the HA by an acidic environment are caused as described above, membrane fusion of the envelope 31 of the virus and the phospholipid film 14 (the phospholipid bilayer) formed in the hole 13a of the graphene film 13 occurs as shown in FIG. 18B.

By the membrane fusion, the contents of the virus interior including RNA, etc., are released to the lower portion of the graphene film 13. By forming a sensor element detecting the contents below the graphene film 13, the membrane fusion of the virus can be detected with high sensitivity. Or, the membrane fusion recited above may be detected by the graphene film 13.

Although the phospholipid film 14 that covers the sensor element in the descriptions recited above is in the state in which a phosphate group is exposed at the surface, it is also possible to suppress the nonspecific adsorption of a contaminant by covering the phosphate group with a hydrophilic group.

FIG. 19 to FIG. 22 are schematic views showing examples of hydrophilic groups covering the phosphate group.

Figure 19:
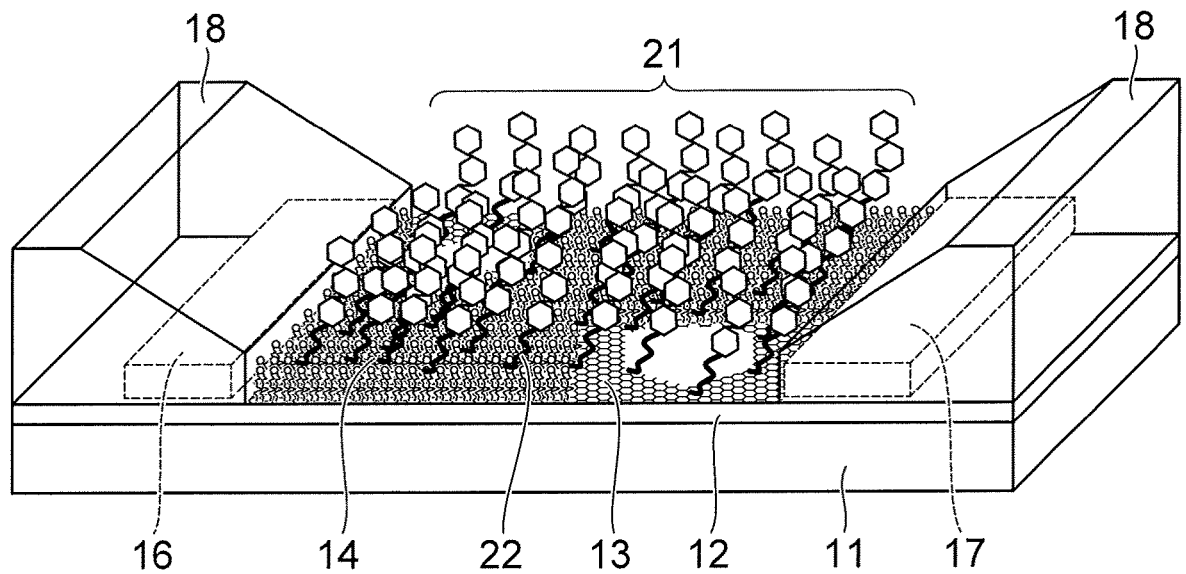
FIG. 19 to FIG. 22 are schematic views showing a protection structure of a phospholipid film of the detection device of the embodiment.

For example, because the sugar chain used as the probe molecule 21 also is hydrophilic as shown in FIG. 19, the nonspecific adsorption of the contaminant can be suppressed by forming the sugar chain probe molecule 21 at high density.

Figure 20:
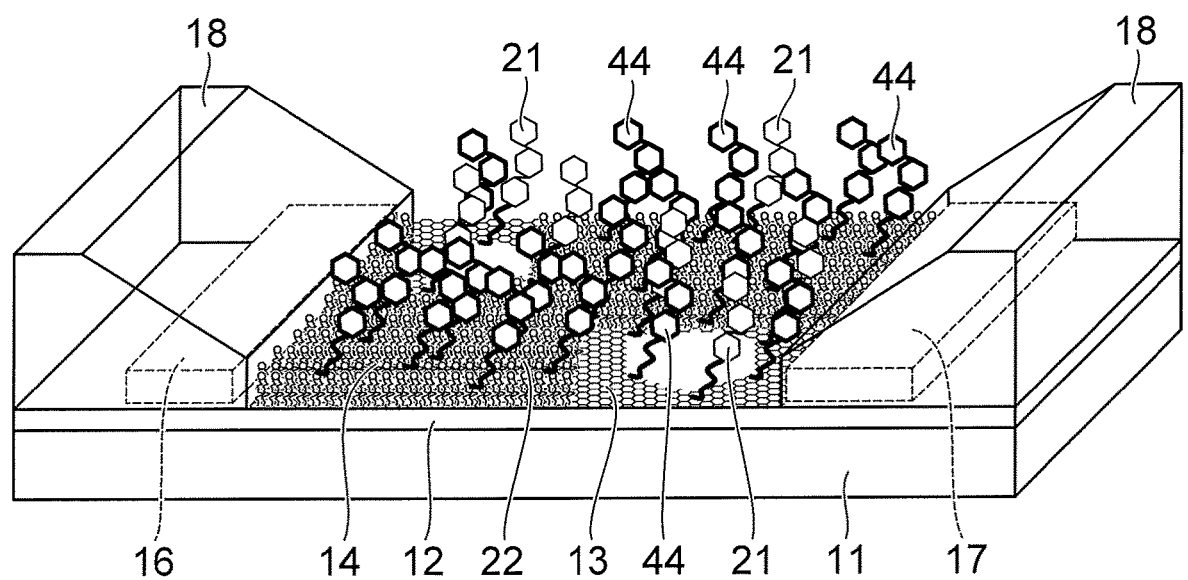

A sugar chain 44 may be formed at high density so that at least a contaminant does not bind as shown in FIG. 20.

Figure 21:
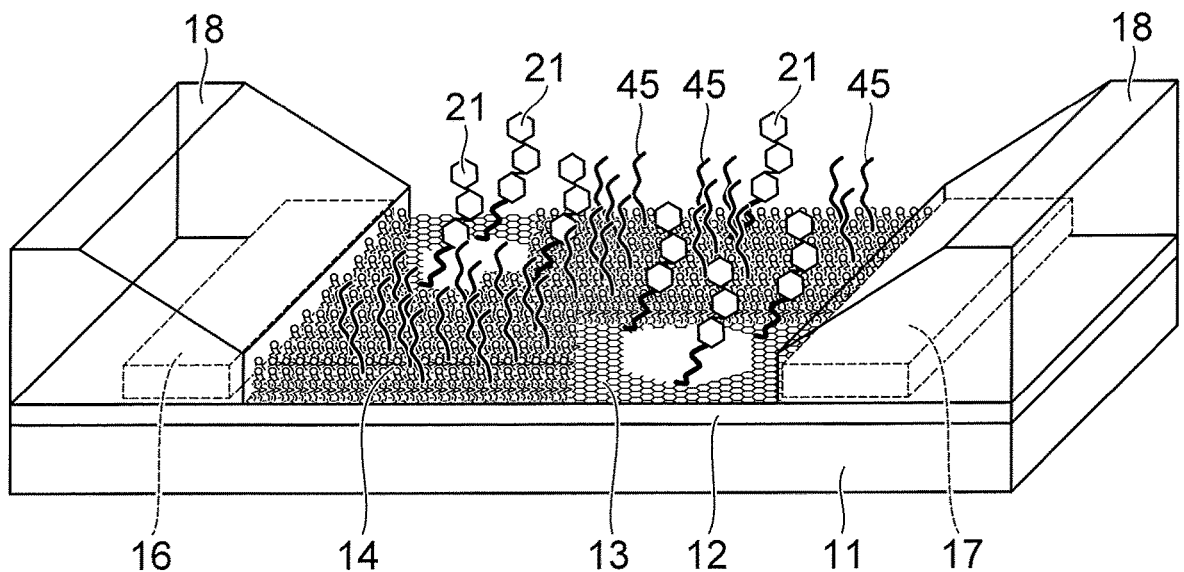

As shown in FIG. 21, for example, a hydrophilic chain polymer 45 such as polyethylene glycol (PEG) may bind to the phosphoric acid site of the phospholipid film 14.

Figure 22:
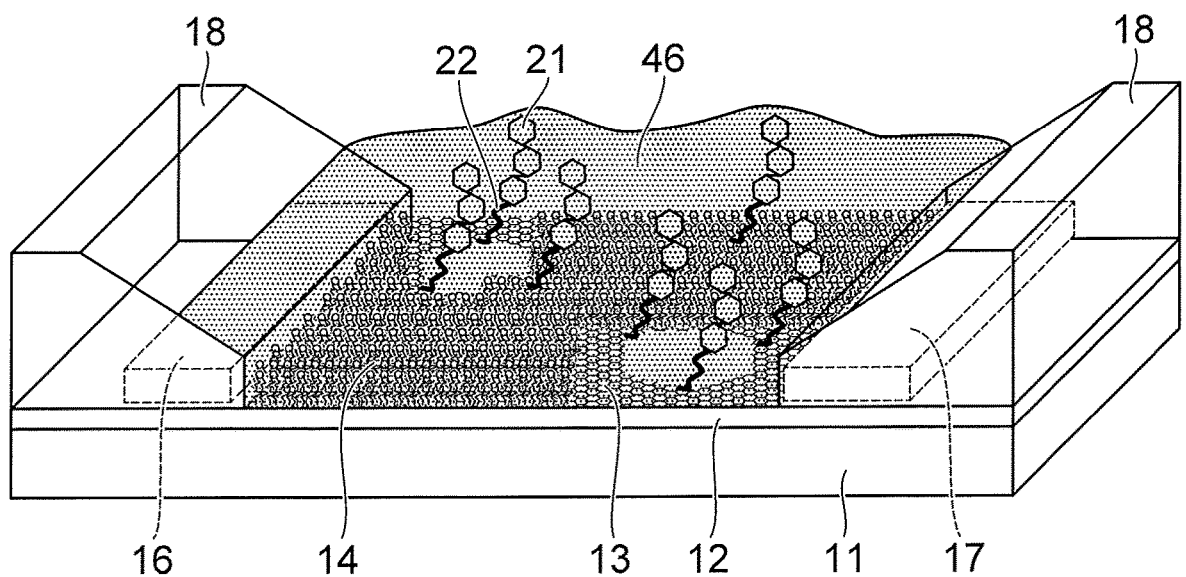

As shown in FIG. 22, for example, a hydrophilic blocking agent 46 such as albumin, etc., may cover the phospholipid film 14.

The charge detection element that is used as the sensor element is not limited to graphene; and carbon nanotubes may be used. The cleaving of HA (the cleaving behavior of HA) is not limited to being detected electrically; and a sensor element that optically or mechanically detects may be used. Other than a carbon-based charge detection element, for example, a surface plasmon resonance element, a SAW (Surface Acoustic Wave) element, an FBAR (Film Bulk Acoustic Resonator) element, a QCM (Quartz Crystal Microbalance) element, an IS-FET (Ion sensitive FET) element, a MEMS (Micro Electro Mechanical System) cantilever element, etc., may be used as the sensor element.

Figure 23A:
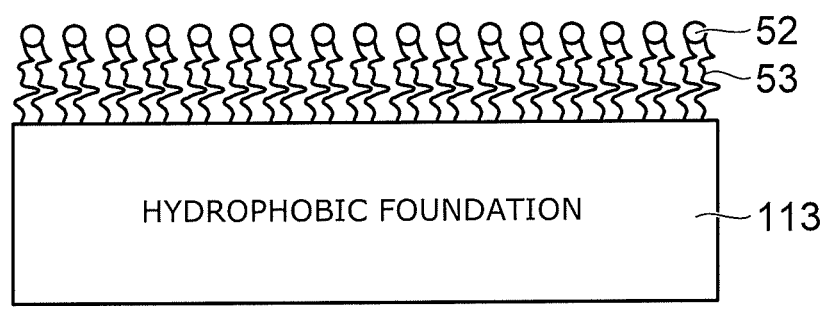
FIG. 23A is a schematic view of a phospholipid film formed on a hydrophobic foundation.
Figure 23B:
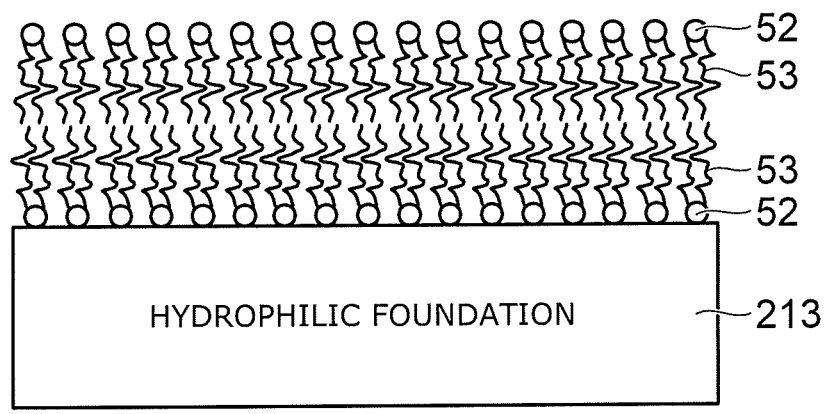
FIG. 23B is a schematic view of a phospholipid film formed on a hydrophilic foundation.

FIG. 23A is a schematic view of the phospholipid film formed on a hydrophobic foundation 113; and FIG. 23B is a schematic view of the phospholipid film formed on a hydrophilic foundation 213.

As shown in FIG. 23A, the phospholipid film is formed as a monolayer film in the case where the surface of the sensor element is the hydrophobic foundation (e.g., the graphene) 113. As shown in FIG. 23B, the phospholipid film is formed as a lipid bilayer in the case where the surface of the sensor element is the hydrophilic foundation 213.

In the case where a mechanical vibration such as QCM is used as the sensor element, the cleaving of the HA can be detected mechanically; therefore, it is not always necessary to form the phospholipid film on the sensor element surface.

According to the embodiments described above, a virus can be detected with high sensitivity by using a probe molecule that binds specifically to a spike protein exposed at the surface of a virus, and by using a sensor element that detects cleaving of the spike protein of the virus bound to the probe molecule. Further, it is possible to specifically detect a designated virus by selecting the probe molecule and the protease cleaving the spike protein.

The detection target is not limited to a virus; and any substance that includes a receptor associating with the probe molecule and has a function in which cleaving of the receptor is expressed can be detected. For example, the detection of a virus-like endoplasmic reticulum such as an exosome also is possible.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modification as would fall within the scope and spirit of the inventions.

What is claimed is:

1. A detection device, comprising:
   a sensor element;
   a phospholipid film provided on a surface of the sensor element; and
   a probe molecule immobilized at the sensor element, the probe molecule associating with a receptor exposed at a surface of a detection target,
   the sensor element detecting the detection target depending on whether fusing or not between the phospholipid film and a surface membrane of the detection target having associated with the probe molecule in an acidic liquid.

2. The device according to claim 1, wherein
   the sensor element is a charge detection element, a surface plasmon resonance element, a SAW (Surface Acoustic Wave) element, a FBAR (Film Bulk Acoustic Resonator) element, a QCM (Quartz Crystal Microbalance) element, an IS-FET (Ion sensitive FET) element, or a MEMS (Micro Electro Mechanical System) cantilever element, and
   the sensor element detects one of a change of a position of the detection target, a change of mobility of the detection target, or a change of a configuration of the receptor due to the cleavage of the receptor.

3. The device according to claim 2, wherein the charge detection element includes graphene or carbon nanotubes.

4. The device according to claim 1, wherein the probe molecule is a sugar chain.

5. The device according to claim 1, wherein
   the detection target is a virus, and
   the receptor is a spike protein.

6. The device according to claim 5, wherein
   the virus is an influenza virus, and
   the spike protein is hemagglutinin.

7. The device according to claim 6, wherein the probe molecule is one of an α-2,6-sugar chain or an α-2,3-sugar chain.

8. The device according to claim 5, wherein
   the device has an injection opening for supplying, onto the sensor element, at least one of:
      a first protease for cleaving the spike protein;
      a protease inhibitor for obstructing cleavage of the spike protein by a second protease mixed in with the detection target; or
      a pH adjusting liquid for promoting membrane fusion after cleavage of the spike protein.

9. The device according to claim 8, wherein
   the first protease is a protease existing in a human also in a place other than the respiratory tract, and
   the protease inhibitor is a trypsin inhibitor.

10. The device according to claim 8, wherein the first protease includes at least one of furin or TMPRSS13/MSPL.

11. The device according to claim 8, wherein the first protease includes at least one of trypsin and TMPRSS2.

12. The device according to claim 5, wherein
    a gel or high viscosity liquid is immobilized on the sensor element,
    the gel or high viscosity liquid is water-soluble, and
    the gel or high viscosity liquid includes at least one of:
       a first protease for cleaving the spike protein;
       a protease inhibitor for obstructing cleavage of the spike protein by a second protease mixed in with the detection target; or
       a pH adjusting liquid for promoting membrane fusion after the cleaving of the spike protein.

13. The device according to claim 12, wherein the gel includes a hydrogel.

14. The device according to claim 12, wherein the high viscosity liquid includes a hydrophilic ionic liquid.

15. The device according to claim 14, wherein the ionic liquid includes a phosphonate compound as an anion.

16. The device according to claim 1, wherein the sensor element includes a target detection element and a reference element, the probe molecule being immobilized at the target detection element, the probe molecule not being immobilized at the reference element.

17. The device according to claim 1, wherein a cleaved receptor of the detection target by a proteolytic enzyme not derived from the detection target penetrates into the phospholipid film and the surface membrane of the detection target fuses the phospholipid film.

18. A detection device, comprising:
    a sensor element;
    a phospholipid film provided on a surface of the sensor element; and
    a probe molecule immobilized at the sensor element, the probe molecule associating with a receptor exposed at a surface of a detection target, wherein
    the sensor element detects the detection target by one of penetration of the receptor of the detection target into the phospholipid film, or fusing between the phospholipid film and a surface membrane of the detection target in an acidic liquid.

19. A detection method, comprising, by a sensor element, detecting a detection target depending on whether fusing or not between a phospholipid film provided on a surface of the sensor element, and a surface membrane of the detection target being associated with a probe molecule immobilized at the sensor element in an acidic liquid.

20. The method according to claim 19, wherein
the detection target is a virus, and
the receptor is a spike protein.

21. The method according to claim 20, comprising:
supplying, onto the sensor element, at least one of
- a first protease for cleaving the spike protein,
- a protease inhibitor for obstructing cleavage of the spike protein by a second protease mixed in with the detection target, or
- a pH adjusting liquid for promoting membrane fusion after cleavage of the spike protein.

* * * * *